United States Patent [19]
Nishioka et al.

[11] Patent Number: 5,907,048
[45] Date of Patent: May 25, 1999

[54] PROCESS FOR PREPARING DIHYDROPYRANE COMPOUND

[75] Inventors: Tohru Nishioka; Shigeyoshi Tanaka; Junji Koshino; Osamu Yamashita, all of Wakayama; Tadahiro Ozawa, Ichikai-machi; Makoto Kohama, Wakayama, all of Japan

[73] Assignee: Kao Corporation, Tokyo, Japan

[21] Appl. No.: 08/941,050

[22] Filed: Sep. 30, 1997

[30] Foreign Application Priority Data

| Oct. 3, 1996 | [JP] | Japan | 8-262702 |
| Jun. 5, 1997 | [JP] | Japan | 9-147559 |
| Jul. 11, 1997 | [JP] | Japan | 9-186307 |

[51] Int. Cl.$^6$ .................................. C07D 309/18
[52] U.S. Cl. ............................................ 549/356
[58] Field of Search ............................... 549/356

[56] References Cited

U.S. PATENT DOCUMENTS

| 3,644,428 | 2/1972 | Inglis | 549/356 |
| 3,681,263 | 8/1972 | Van Der Linde et al. | 549/356 |
| 5,162,551 | 11/1992 | Broekhof et al. | 549/356 |

FOREIGN PATENT DOCUMENTS

| 0 325 000 | 7/1989 | European Pat. Off. . |
| 1 942 387 | 3/1970 | Germany . |
| 1-238578 | 9/1989 | Japan . |
| 655 932 A5 | 5/1986 | Switzerland . |
| 1 205 157 | 9/1970 | United Kingdom . |
| 1 337 263 | 11/1973 | United Kingdom . |

OTHER PUBLICATIONS

Junji Inanaga, et al., New J. Chem., vol. 19, pp. 707–712, 1995, "Achiral and Chiral Lanthanide(III) Salts of Superacids as Novel Lewis Acid Catalysts in Organic Synthesis".
Megumu Munakata, et al., Inorganic Chemistry, vol. 24, No. 11, pp. 1638–1643, 1985, "Classification of Solvents Bases on Their Coordination Power to Nickel(II) Ion. A New Measure for Solvent Donor Ability".
Comprehensive Organic Synthesis, vol. 5, Pergamon Press (1991), pp. 431–432.
Arm. Khm. Zh. (1976), vol. 29, No. 3 pp. 276–277.
Junji Inanaga, et al., "Scandium (III) Perfluorooctanesulfonate [Sc(OPf)3]: A Novel Catalyst for the Hetero Diels–Alder Reaction of Aldehydes with Non–Activated Dienes", New Journal of Chemistry, (1995), vol. 19, No. 707, pp. 2–11.
Varinder. K. Aggarwal, et al., "Trifluoromethanesulfonic Acid, An Efficient Catalyst for the Hetero Diels–Alder Reaction and an Improved Synthesis of Mefrosol.", Tetrahedron Letters, vol. 38, No. 14, Apr. 7, 1997, pp. 2569–2572.

*Primary Examiner*—Bernard Dentz
*Attorney, Agent, or Firm*—Oblon, Spivak, McClelland, Maier & Neustadt, P.C.

[57] ABSTRACT

To provide a simple process for economically preparing a dihydropyrane compound at a high productivity and a high reaction yield.

To use a compound selected from the group consisting of a base and a compound (VIII) having a weaker coordination power to the Lewis acid than the aldehyde compound and having an activity to dissolve the Lewis acid, coordinated by the compound (VIII), in a solvent as a co-catalyst in reacting aldehyde with a diene compound in the presence of a Lewis acid to prepare a 5,6-dihydro-2H-pyrane compound represented by formula (III):

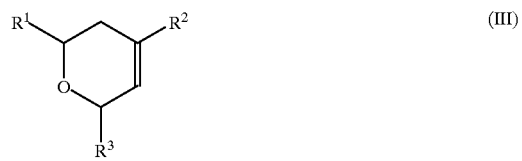

in which $R^1$ represents a hydrogen atom, an alkyl group having 1 to 12 carbon atoms, aryl group which may be substituted with alkyl group, having 6 to 12 total carbon atoms; $R^2$ and $R^3$ represent a hydrogen atom or an alkyl group having 1 to 6 carbon atoms.

16 Claims, No Drawings

PROCESS FOR PREPARING DIHYDROPYRANE COMPOUND

FIELD OF THE INVENTION

The present invention relates to a high selective process for preparing a dihydropyrane compound. More specifically, the present invention relates to a process for preparing a dihydropyrane compound at a high selectivity and a high reaction yield.

ARTS IN THE BACKGROUND

A dihydropyrane compound is an important industrial raw material for perfumes. For example, α-phenyl-dihydropyrane can be converted to 5-phenylpentanol which is particularly important as perfume by reductive ring opening of the pyrane ring (Swiss Patent 655932). Further, dihydropyrane compounds such as 6-phenyl-4-methyl-5,6-dihydro-2H-pyrane, 6-phenyl-2,4-dimethyl-5,6-dihydro-2H-pyrane and 6-butyl-2,4-dimethyl-5,6-dihydro-2H-pyrane are useful themselves (U.S. Pat. No. 3,681,263 and Arm. Khm. Zh. (1976), 29 (3), p. 276 to 277).

As described in the literatures described above, these dihydropyrane compounds can be obtained in the form of a mixture of the double bond isomers by reacting aldehyde compounds such as benzaldehyde and valeraldehyde (pentanal) with 3-butene-1-ol compounds such as isoprenol in the presence of a catalytic amount of an acid. However, 3-butene-1-ol compounds are expensive, and therefore a method for preparing these dihydropyrane compounds from readily available and inexpensive raw materials has been desired.

A method by a hetero Diels-Alder reaction of aldehyde compounds with conjugated diene compounds is known as such a method. In this case, conjugated diene compounds such as isoprene and 2-methylpentadiene are readily available. In general, however, in this kind of the hetero Diels-Alder reaction, the products have been able to obtain at practical reaction yield only when high reactive aldehyde compounds such as glyoxylic ester and trichloroacetaldehyde are used (Comprehensive Organic Synthesis, Vol. 5, p. 431 Pergamon Press 1991).

A reaction of aldehyde compounds with diene compounds using a Lewis acid as a catalyst is available as an improving method thereof. For example, a method in which aluminum chloride or tin tetrachloride is used as a Lewis acid catalyst and an aliphatic or aromatic nitro compound is further used as a co-catalyst is known (JP-A 1-238578). In this method, however, wastes are produced in large quantities after the reaction, and the reaction yield is as low as about 50%. Accordingly, this method has not yet been sufficiently satisfactory in the viewpoint of reaction yield and productivity. In recent year, known as well is a method in which rare earth metal perfluoroalkanesulfonate such as scandium perfluorate as a catalyst is used to carry out the hetero Diels-Alder reaction (New Journal of Chemistry, 1995, vol. 19, 707). However, this method uses an expensive catalyst and therefore is uneconomical and industrially unsuitable.

Tetrahedron Letters vol. 38, No. 14, pages 2569–2572, published on, Apr. 7th, 1997, discloses reaction of an aromatic aldehyde with an excess amount of a diene with a catalsyt of trifluoromethanesulfonic acid.

Accordingly, an object of the present invention is to provide a simple process for preparing a dihydropyrane compound by the hetero Diels-Alder reaction of an aldehyde compound with a diene compound, in view of a high productivity, a high reaction yield and an economic save.

DISCLOSURE OF THE INVENTION

Intensive investigations continued by the present inventors in order to solve the problems described above have resulted in finding that a dihydropyrane compound can easily be prepared at a high productivity and a high reaction yield by using a specific compound as a co-catalyst in preparing the dihydropyrane compound from an aldehyde compound and a diene compound in the presence of a Lewis acid catalyst, and thus coming to complete the present invention.

The present invention provides a process for preparing a dihydropyrane compound (III) having the formula (III):

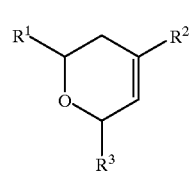

(III)

in which $R^1$ represents a hydrogen atom, an alkyl group or alkenyl group having 1 to 12 carbon atoms, a cycloalkyl group which may be substituted with alkyl group, having 3 to 12 total carbon atoms or an aryl group which may be substituted with alkyl group or alkoxy group, having 6 to 12 total carbon atoms; $R^2$ and $R^3$ may be same or different and each represents a hydrogen atom or an alkyl group or alkenyl group having 1 to 6 carbon atoms, which comprises the step of reacting an aldehyde compound (I) having the formula (I):

in which $R^1$ is defined as above, with a diene compound (II) having the formula (II):

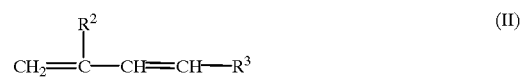

in which $R^2$ and $R^3$ are defined as above, in the presence of a Lewis acid and at least one co-catalyst selected from the group consisting of a base and a compound (VIII) having a weaker coordination power to the Lewis acid than the aldehyde compound (I) and having an activity to dissolve the Lewis acid, coordinated by the compound (VIII), in a solvent, provided that when the compound (VIII) is solely used, it is not any nitro compound.

The present invention provides a process in which the co-catalyst is a base, a process in which the co-catalyst is a compound (VIII), or a process in which the co-catalyst is a combination of a base with a compound (VIII), as a mode for carrying out.

Preferably, the co-catalyst is a compound (VIII) selected from the group consisting of an aliphatic or aromatic ester compound, a chloro-acetic ester compound, an ether compound, a ketone compound and a carbonate compound.

Preferably, the Lewis acid is selected from the group consisting of aluminum chloride, tin tetrachloride, iron trichloride, titanium trichloride, titanium tetrachloride and boron trifluoride.

Preferably, the base is used in an amount of 0.01 to 1 mole per 1 mole of the Lewis acid.

Preferably, the compound (VIII) is used in an amount of 0.1 to 10 moles per 1 mole of the Lewis acid.

Preferably, the base is used in an amount of 0.01 to 1 mole per 1 mole of the Lewis acid and the compound (VIII) is used in an amount of 0.1 to 10 moles per 1 mole of the Lewis acid.

Preferably, the co-catalyst is a combination of a base with a nitro compound as the compound (VIII).

Preferably, the Lewis acid is boron trifluoride and the co-catalyst is an amine compound as the base.

Preferably, the Lewis acid is aluminum chloride and the co-catalyst is methyl benzoate as the compound (VIII).

The invention as defined above is an improvement of the hetero Diels-Alder reaction, obtained by use of a catalyst and combined two co-catalysts, in view of a high reaction yield, a high productivity and an economic save.

MODE FOR CARRYING OUT THE INVENTION

The embodiment of the present invention shall be explained below in detail.

In the aldehyde compound represented by formula (I) used in the preparing process of the present invention, $R^1$ represents a hydrogen atom, an alkyl group or alkenyl group having 1 to 12 carbon atoms, a cycloalkyl group which may be substituted with alkyl group, having 3 to 12 total carbon atoms or an aryl group which may be substituted with alkyl group or alkoxy group, having 6 to 12 total carbon atoms, preferably an alkyl group having 3 to 12 carbon atoms or an aryl group which may be substituted with alkyl group, having 6 to 12 total carbon atoms, particularly preferably an aryl group having 6 to 10 total carbon atoms, and further particularly preferably a phenyl group or an o-, m- or p-tolyl group.

Specific examples of the aldehyde compound represented by formula (I) include benzaldehyde, o-, m- or p-tolualdehyde, naphthoaldehyde, butyraldehyde, valeraldehyde, caproaldehyde, heptaldehyde, caprylic aldehyde, nonyl aldehyde and lauraldehyde.

In the diene compound represented by formula (II) used in the preparing process of the present invention, $R^2$ and $R^3$ may be same or different and each represents a hydrogen atom or an alkyl group or alkenyl group having 1 to 6 carbon atoms, preferably a hydrogen atom or methyl group.

Specific examples of the diene compound represented by formula (II) include isoprene, 2-methyl-1,3-pentadiene, butadiene, and 1,3-pentadiene, and isoprene and 2-methyl-1,3-pentadiene are particularly preferred.

In the present invention, the reaction ratio of the aldehyde compound to the diene compound is preferably 5/1 to 1/5, particularly preferably 2/1 to 1/2 in terms of molar ratio of diene/aldehyde.

In the present invention, the Lewis acid used as the catalyst shall not specifically be restricted. Aluminum chloride, tin tetrachloride, iron trichloride, titanium trichloride, titanium tetrachloride and boron trifluoride are preferred. The Lewis acid catalyst is used in an amount of 0.001 mole or more, suitably 0.005 to 0.8 mole, or 0.005 to 0.4 mole, per 1 mole of the aldehyde compound.

Or the Lewis acid used as the catalyst shall not specifically be restricted. Aluminum chloride, tin tetrachloride, and boron trifluoride are preferred. The Lewis acid catalyst is used in an amount of 0.001 mole or more, suitably 0.005 to 0.4 mole per 1 mole of the aldehyde compound.

In the present invention, the compound (VIII) having a weaker coordination power to the Lewis acid than the aldehyde compound represented by formula (I) and having an activity to dissolve the Lewis acid, coordinated by the compound (VIII), in a solvent is used in combination with the base, as the co-catalyst.

The compound (VIII) used in the present invention is at least one compound selected from the group consisting of an aliphatic or aromatic ester compound, a chloroacetic ester compound, an ether compound, a ketone compound, a carbonate compound and a nitro compound.

In the present invention, the coordination power to the Lewis acid can be estimated by an amount of a heat of forming a complex with the Lewis acid. The measured values described in Friedel-Crafts and Related Reaction, vol. 1, 601 (1963) by J. A. Olah can be used as the heat of formation. Or, an AM1 method which is a semi-empirical molecular orbital method package MOPAC 93 may be used to calculate it.

Specific examples of the aliphatic or aromatic ester compounds used as the compound (VIII) in the present invention include methyl acetate, ethyl acetate, propyl acetate, octyl acetate, phenyl acetate, methyl benzoate, ethyl benzoate, propyl benzoate, diethyl terephthalate and ethyl p-cholorobenzoate. Specific examples of the chloroacetic ester compounds include methyl monochloroacetate, ethyl monochloroacetate, methyl dichloroacetate, ethyl dichloroacetate, methyl trichloroacetate and ethyl trichloroacetate. Specific examples of the ether compounds include anisole and diphenyl ether. Specific examples of the ketone compounds include acetophenone and benzophenone. Specific examples of the carbonate compounds include dimethyl carbonate and ethylene carbonate. Specific examples of the nitro compounds include nitromethane, nitroethane, nitropropane, nitrobenzene and nitrocyclohexane. Among them, a lower alkyl benzoate, a lower alkyl acetate, a lower alkyl monochloroacetate, anisole, benzophenone, ethylene carbonate, nitropropane and nitromethane are particularly preferred.

In the present invention, the use amount of the compound (VIII) preferably 0.1 to 10 moles, still preferably 0.5 to 2.0 moles per 1 mole of the Lewis acid.

The base or a basic compound used as the co-catalyst in the present invention may be any ones as long as they have a property capable of capturing acidic compounds and include, for example, amine compounds, strong alkaline salts of weak acids such as organic carboxylic acids and phosphoric acid (sodium acetate, disodium hydrogenphosphate and the like), and oxides, hydroxides, carbonates and bicarbonates of alkaline metals and alkaline earth metals (calcium oxide, magnesium oxide, sodium hydroxide, sodium carbonate, sodium bicarbonate and the like). Amine compounds are preferred from the viewpoint of a solubility into the raw materials. To be specific, amine compounds include ammonia, aliphatic amine compounds, alicyclic amine compounds, aromatic amine compounds and heterocyclic compounds having nitrogen atoms, preferably aliphatic amine compounds or pyridine. These amine compounds include primary, secondary and tertiary amine compounds. Among them, tertiary amine compounds are preferred. In addition, these amine compounds may be either of monoamine compounds and polyamine compounds. Among them, monoamine compounds are preferred. Further, the total number of carbon atoms contained in these amine compounds is preferably 30 or less (including ammonia having zero carbon atom), more preferably 3 to 20, and particularly preferably 6 to 12.

Specific examples of these amine compounds include the following ones.

Aliphatic primary amine compounds

Methylamine, ethylamine, propylamine, isopropylamine, butylamine, amylamine, hexylamine, heptylamine, octylamine, nonylamine, decylamine, undecylamine, dodecylamine, and the like.

Aliphatic secondary amine compounds

Dimethylamine, diethylamine, dipropylamine, diisopropylamine, dibutylamine, diamylamine, and the like.

Aliphatic tertiary amine compounds

Trimethylamine, triethylamine, tripropylamine, tributylamine, diisopropylethylamine, diethylmethylamine, diethylpropylamine, diisopropylmethylamine, and the like.

Alicyclic amine compounds

Cyclopropylamine, cyclobutylamine, cyclopentylamine, cyclohexylamine, and the like.

Aromatic amine compounds

Aniline, methylaniline, dimethylaniline, ethylaniline, diethylaniline, toluidine, benzylamine, diphenylamine, naphthylamine, and the like.

Heterocyclic amine compounds

Pyridine and the like.

Polyamine compounds

Ethylenediamine, diethylenetriamine, propylenediamine, dipropylenetriamine, and the like.

In the present invention, the use amount of the base is preferably 0.01 to 1 mole, more preferably 0.01 to 0.4 mole per 1 mole of the Lewis acid.

In the present invention, the reaction yield can be raised by 10 to 20% as compared with, for example, the case where only the compound (VIII) is used by using the preceding compound (VIII) in combination with the base, as the co-catalyst.

In the present invention, the compound (VIII) described above solely, the base solely, or a combination of the compound (VIII) with the base can be used as the co-catalyst.

In the present invention, when the compound (VIII) is solely used, it is not any nitro compound.

The reaction in the present invention can be carried out either without using a solvent or using a solvent. Hydrocarbon base solvents and chlorine base solvents are preferred as the solvent used in the present invention. The hydrocarbon base solvents include benzene, toluene, xylene, pentane, hexane, cyclohexane and petroleum ether. The chlorine base solvents include chlorobenzene, dichloromethane and tetrachloroethylene. These solvents may be used either alone or in a mixture of two or more kinds thereof. They are used preferably in an amount of 50% by weight or more, particularly preferably 100% by weight or more based on the weight of aldehyde compound.

In the present invention, the optimum reaction temperature depends on the reactivity of aldehyde compound with the diene compound, the kinds of the catalyst and the co-catalyst used, the use amounts thereof and the presence and the property of the solvent In general, it is −30 to 100° C., particularly suitably −20 to 70° C.

In the present reaction, when a compound (VIII) solely or a combination of a base with a compound (VIII) is used as a co-catalyst, a method for mixing the aldehyde compound, the diene compound, the catalyst and the co-catalyst shall not specifically be restricted, and a conventional method which can advantageously be used is a method in which a mixture of the aldehyde compound, the diene compound and the solvent is added dropwise to a mixture of the catalyst, the co-catalyst and the solvent while keeping the desired temperatures. The reaction is carried out preferably in the absence of water and oxygen.

In the present reaction, when a base is solely used as a co-catalyst, a method for mixing the aldehyde compound, the diene compound, the catalyst and the co-catalyst shall not specifically be restricted, and a conventional method which can advantageously be used is a method in which a mixture of the catalyst and the co-catalyst is added dropwise to a mixture of the aldehyde compound, the diene compound and the solvent while keeping the desired temperatures under strong stirring. The reaction is carried out preferably in the absence of water and oxygen.

The present invention shall be explained below in further detail with reference to examples, but the present invention shall not be restricted to these examples.

EXAMPLE 1

Preparation of 6-phenyl-4-methyl-5,6-dihydro-2H-pyrane represented by the following formula (IV)

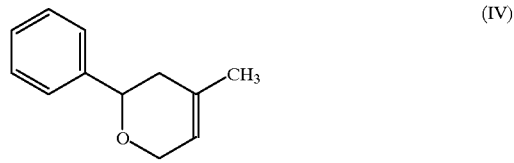

4.66 g (44.0 mmol) of benzaldehyde, 3.00 g (44.1 mmol) of isoprene and 5 ml of dried toluene were fed into a 30 ml pressure glass vessel replaced with nitrogen, and then a mixture of 0.90 g (6.3 mmol) of $BF_3.O(C_2H_5)_2$, 0.18 g (1.4 mmol) of N,N-diisopropylethylamine and 5 ml of dried toluene was added dropwise in 30 minutes while vigorously stirring at about 0° C. After stirring the mixture for 8.5 hours, it was cooled down and then poured into ice and water. The organic layer was separated, and the aqueous layer was washed with hexane. The collected organic layer was washed with an aqueous solution of sodium hydrogen carbonate and then with a saturated saline solution. The solvents were distilled off, and the residue was distilled under reduced pressure, whereby 5.99 g (yield: 78%) of the desired dihydropyrane compound was obtained.

EXAMPLE 2

Preparation of 6-phenyl-4-methyl-5,6-dihydro-2H-pyrane represented by the formula (IV) described above 4.66 g (44.0 mmol) of benzaldehyde, 3.00 g (44.1 mmol) of isoprene and 5 ml of dried toluene were fed into a 30 ml pressure glass vessel replaced with nitrogen, and then a mixture of 0.94 g (6.6 mmol) of $BF_3.O(C_2H_5)_2$, 0.11 g (1.3 mmol) of sodium acetate and 5 ml of dried toluene was added dropwise in 30 minutes while vigorously stirring at about 0° C. After stirring the mixture for 4.5 hours, it was cooled down and then poured into ice and water. The organic layer was separated, and the aqueous layer was washed with hexane. The collected organic layer was washed with an aqueous solution of sodium hydrogen carbonate and then with a saturated saline solution. The solvents were distilled off, and the residue was distilled under reduced pressure, whereby 4.62 g (yield: 60%) of the desired dihydropyrane compound was obtained.

EXAMPLE 3

Preparation of 6-phenyl-4-methyl-5,6-dihydro-2H-pyrane represented by the formula (IV) described above 4.66 g (44.0 mmol) of benzaldehyde, 3.00 g (44.1 mmol) of isoprene and 5 ml of dried toluene were fed into a 30 ml pressure glass vessel replaced with nitrogen, and then a mixture of 0.94 g (6.6 mmol) of BF$_3$.O(C$_2$H$_5$)$_2$, 0.10 g (1.3 mmol) of pyridine and 5 ml of dried toluene was added dropwise in 30 minutes while vigorously stirring at about 0° C. After stirring the mixture for 8 hours, it was cooled down and then poured into ice and water. The organic layer was separated, and the aqueous layer was washed with hexane. The collected organic layer was washed with an aqueous solution of sodium hydrogen carbonate and then with a saturated saline solution. The solvents were distilled off, and the residue was distilled under reduced pressure, whereby 5.36 g (yield: 70%) of the desired dihydropyrane compound was obtained.

EXAMPLE 4
Preparation of 6-phenyl-4-methyl-5,6-dihydro-2H-pyrane represented by the formula (IV) described above 4.66 g (44.0 mmol) of benzaldehyde, 3.00 g (44.1 mmol) of isoprene and 5 ml of dried toluene were fed into a 30 ml pressure glass vessel replaced with nitrogen, and then a mixture of 0.36 g (2.2 mmol) of AlCl$_3$, 0.057 g (0.44 mmol) of N,N-diisopropylethylamine and 5 ml of dried toluene was added dropwise in 30 minutes while vigorously stirring at about 0° C. After stirring the mixture for 15 hours, it was cooled down and then poured into ice and water. The organic layer was separated, and the aqueous layer was washed with hexane. The collected organic layer was washed with an aqueous solution of sodium hydrogen carbonate and then with a saturated saline solution. The solvents were distilled off, and the residue was distilled under reduced pressure, whereby 5.36 g (yield: 70%) of the desired dihydropyrane compound was obtained.

EXAMPLE 5
Preparation of 6-phenyl-2,4-dimethyl-5,6-dihydro-2H-pyrane represented by the following formula (V)

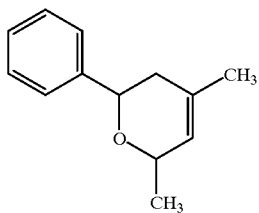

(V)

4.66 g (44.0 mmol) of benzaldehyde, 3.57 g (44.1 mmol) of 2-methyl-1,3-pentadiene and 5 ml of dried toluene were fed into a 30 ml pressure glass vessel replaced with nitrogen, and then a mixture of 0.90 g (6.3 mmol) of BF$_3$.O(C$_2$H$_5$)$_2$, 0.18 g (1.4 mmol) of N,N-diisopropylethylamine and 5 ml of dried toluene was added dropwise in 30 minutes while vigorously stirring at about 0° C. After stirring the mixture for 12 hours, it was cooled down and then poured into ice and water. The organic layer was separated, and the aqueous layer was washed with hexane. The collected organic layer was washed with an aqueous solution of sodium hydrogen carbonate and then with a saturated saline solution. The solvents were distilled off, and the residue was distilled under reduced pressure, whereby 5.96 g (yield: 72%) of the desired dihydropyrane compound was obtained.

EXAMPLE 6
Preparation of 6-p-tolyl-4-methyl-5,6-dihydro-2H-pyrane represented by the following formula (VI)

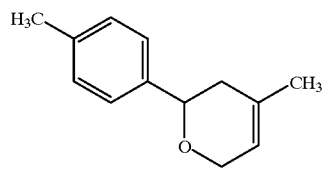

(VI)

5.28 g (44.0 mmol) of p-tolualdehyde, 3.00 g (44.1 mmol) of isoprene and 5 ml of dried toluene were fed into a 30 ml pressure glass vessel replaced with nitrogen, and then a mixture of 0.90 g (6.3 mmol) of BF$_3$.O(C$_2$H$_5$)$_2$, 0.18 g (1.4 mmol) of N,N-diisopropylethylamine and 5 ml of dried toluene was added dropwise in 30 minutes while vigorously stirring at about 0° C. After stirring the mixture for 15 hours, it was cooled down and then poured into ice and water. The organic layer was separated, and the aqueous layer was washed with hexane. The collected organic layer was washed with an aqueous solution of sodium hydrogen carbonate and then with a saturated saline solution. The solvents were distilled off, and the residue was distilled under reduced pressure, whereby 6.20 g (yield: 75%) of the desired dihydropyrane compound was obtained.

EXAMPLE 7
Preparation of 6-n-butyl-4-methyl-5,6-dihydro-2H-pyrane represented by the following formula (VII)

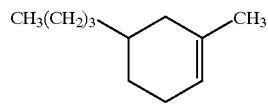

(VII)

3.39 g (44.0 mmol) of valeraldehyde, 3.00 g (44.1 mmol) of isoprene and 5 ml of dried toluene were fed into a 30 ml pressure glass vessel replaced with nitrogen, and then a mixture of 0.90 g (6.3 mmol) of BF$_3$.O(C$_2$H$_5$)$_2$, 0.18 g (1.4 mmol) of N,N-diisopropylethylamine and 5 ml of dried toluene was added dropwise in 30 minutes while vigorously stirring at about 0° C. After stirring the mixture for 15 hours, it was cooled down and then poured into ice and water. The organic layer was separated, and the aqueous layer was washed with hexane. The collected organic layer was washed with an aqueous solution of sodium hydrogen carbonate and then with a saturated saline solution. The solvents were distilled off, and the residue was distilled under reduced pressure, whereby 4.66 g (yield: 73%) of the desired dihydropyrane compound was obtained.

EXAMPLE 8
Preparation of 6-phenyl-4-methyl-5,6-dihydro-2H-pyrane represented by the formula (IV) described above 3.20 g (24 mmol) of aluminum chloride was fed into a 200 ml four neck flask equipped with a condenser, a thermometer and a stirrer and then this vessel was replaced with nitrogen. 40 ml of toluene and 3.27 g (24 mmol) of methyl benzoate were added thereto at room temperatures. This mixture was cooled down to 0° C., and a mixed solution of 12.70 g (120 mmol) of benzaldehyde, 19.00 g (280 mmol) of isoprene and 50 ml of toluene was added dropwise in one hour while keeping the temperatures of 0 to 5° C. After finishing adding, the mixture was stirred for 10 minutes. Then, it was cooled down and poured into ice and water. The layers were separated, and the aqueous layer was washed with some quantity of toluene. The collected organic layer was washed with an aqueous solution of sodium hydrogen carbonate and then with a saturated saline solution. The solvent was distilled off, and the residue was distilled under reduced pressure, whereby 15.9 g (yield: 76%) of desired dihydropyrane was obtained.

EXAMPLE 9
Preparation of 6-phenyl-4-methyl-5,6-dihydro-2H-pyrane represented by the formula (IV) described above 3.20 g (24 mmol) of aluminum chloride was fed into a 200 ml four neck flask equipped with a condenser, a thermometer and a stirrer and then this vessel was replaced with nitrogen. 40 ml of toluene and 3.27 g (24 mmol) of methyl benzoate were added thereto at room temperatures. This mixture was cooled down to 0° C., and a mixed solution of 12.70 g (120 mmol) of benzaldehyde, 10.7 g (156 mmol) of isoprene and 50 ml of toluene was added dropwise in one hour while keeping the temperatures of 0 to 5° C. After finishing adding, the mixture was stirred for 10 minutes. Then, it was cooled down and poured into ice and water. The layers were separated, and the aqueous layer was washed with some quantity of toluene. The collected organic layer was washed with an aqueous solution of sodium hydrogen carbonate and then with a saturated saline solution. The solvent was distilled off, and the residue was distilled under reduced pressure, whereby 14.4 g (yield: 70%) of desired dihydropyrane was obtained.

EXAMPLES 10 to 14
6-Phenyl-4-methyl-5,6-dihydro-2H-pyrane represented by the formula (IV) described above was obtained at the yields shown in Table 1 respectively in the same manner as in Example 8, except that the co-catalyst was changed as shown in Table 1.

TABLE 1

| | co-catalyst | yield (%) |
| --- | --- | --- |
| Example 10 | methyl monochloroacetate | 79 |
| Example 11 | anisole | 88 |
| Example 12 | methyl acetate | 60 |
| Example 13 | benzophenone | 65 |
| Example 14 | ethylene carbonate | 68 |

EXAMPLE 15
Preparation of 6-phenyl-2,4-dimethyl-5,6-dihydro-2H-pyrane represented by the formula (V) described above The reaction was carried out in the same manner as in Example 8, except that 23 g (280 mmol) of 2-methyl-1,3-pentadiene was substituted for isoprene, whereby 16.1 g (yield: 72%) of desired dihydropyrane was obtained.

EXAMPLE 16
Preparation of 6-p-tolyl-4-methyl-5,6-dihydro-2H-pyrane represented by the formula (VI) described above:

The reaction was carried out in the same manner as in Example 8, except that 14.4 g (120 mmol) of p-tolualdehyde was substituted for benzaldehyde, whereby 16.8 g (yield: 75%) of desired dihydropyrane was obtained.

EXAMPLE 17
Preparation of 6-n-butyl-4-methyl-5,6-dihydro-2H-pyrane represented by the formula (VII) described above The reaction was carried out in the same manner as in Example 8, except that 10.3 g (120 mmol) of valeraldehyde was substituted for benzaldehyde, whereby 13.5 g (yield: 73%) of desired dihydropyrane was obtained.

EXAMPLE 18
Preparation of 6-phenyl-4-methyl-5,6-dihydro-2H-pyrane represented by the formula (IV) described above 6.40 g (48 mmol) of aluminum chloride was fed into a 200 ml four neck flask equipped with a condenser, a thermometer and a stirrer and then this vessel was replaced with nitrogen. 80 ml of toluene and 3.27 g (24 mmol) of methyl benzoate were added thereto at room temperatures. This mixture was cooled down to 0° C., and 0.76 g (9.6 mmol) of pyridine was added. Then, a mixed solution of 6.35 g (60 mmol) of benzaldehyde, 5.35 g (79 mmol) of isoprene and 25 ml of toluene was added dropwise in 3 hours while keeping the temperatures of 0 to 5° C. After finishing adding, the mixture was further stirred for 10 minutes. Then, it was poured into ice and water to stop the reaction, and the organic layer was recovered. The aqueous layer was extracted with toluene, and the collected organic layer was washed with an aqueous solution of sodium hydrogen carbonate and then with a saturated saline solution. The solvent was distilled off, and the residue was distilled under reduced pressure, whereby 8.77 g (yield: 84%) of desired dihydropyrane was obtained.

EXAMPLE 19
Preparation of 6-phenyl-4-methyl-5,6-dihydro-2H-pyrane represented by the formula (IV) described above 3.20 g (24 mmol) of aluminum chloride was fed into a 200 ml four neck flask equipped with a condenser, a thermometer and a stirrer and then this vessel was replaced with nitrogen. 40 ml of toluene and 2.14 g (24 mmol) of 2-nitropropane were added thereto at room temperatures. This mixture was cooled down to 0° C., and 0.12 g (1.2 mmol) of triethylamine was added. Then, a mixed solution of 7.11 g (67 mmol) of benzaldehyde, 10.7 g (156 mmol) of isoprene and 50 ml of toluene was added dropwise in 1.5 hour while keeping the temperatures of 0 to 5° C. After finishing adding, the mixture was further stirred for 10 minutes. Then, it was poured into ice and water to stop the reaction, and the organic layer was recovered. The aqueous layer was extracted with toluene, and the collected organic layer was washed with an aqueous solution of sodium hydrogen carbonate and then with a saturated saline solution. The solvent was distilled off, and the residue was distilled under reduced pressure, whereby 9.21g (yield: 79%) of desired dihydropyrane was obtained.

EXAMPLE 20
Preparation of 6-phenyl-4-methyl-5,6-dihydro-2H-pyrane represented by the formula (IV) described above 6.40 g (48 mmol) of aluminum chloride was fed into a 200 ml four neck flask equipped with a condenser, a thermometer and a stirrer and then this vessel was replaced with nitrogen. 80 ml of toluene and 3.27 g (24 mmol) of methyl benzoate were added thereto at room temperatures. This mixture was cooled down to 0° C., and then a mixed solution of 6.35g (60mmol) of benzaldehyde, 5.35 g (79 mmol) of isoprene and 25 ml of toluene was added dropwise in 3 hours while keeping the temperatures of 0 to 5° C. After finishing adding, the mixture was further stirred for 10 minutes. Then, it was poured into ice and water to stop the reaction, and the organic layer was recovered. The aqueous layer was extracted with toluene, and the collected organic layer was washed with an aqueous solution of sodium hydrogen carbonate and then with a saturated saline solution. The solvent was distilled off, and the residue was distilled under reduced pressure, whereby 6.79 g (yield: 65%) of desired dihydropyrane was obtained.

Comparative Example 1
Preparation of 6-phenyl-4-methyl-5,6-dihydro-2H-pyrane represented by the formula (IV) described above 6.4 g (47 mmol) of aluminum chloride and 60 g of toluene were fed into a 200 ml four neck flask equipped with a condenser, a thermometer and a stirrer. This mixture was cooled down to about 5° C., and 3.8 g (36 mmol) of benzaldehyde was added in 5 minutes. Then, a mixture of 8.9 g (84 mmol) of benzaldehyde, 17.6 g (260 mmol) of isoprene and 25 g of toluene was added dropwise in 30 minutes while stirring thoroughly at 5° C. After further stirring the mixture for 10 minutes at 15° C., it was cooled down and then poured into ice and water. The organic layer was separated, and the aqueous layer was washed with hexane. The collected organic layer was washed with an aqueous solution of sodium hydrogen carbonate and then with a saturated saline solution. The solvents were distilled off, and the residue was distilled under reduced pressure, whereby 10.1 g (yield: 48%) of desired dihydropyrane was obtained.

Comparative Example 2
Preparation of 6-phenyl-4-methyl-5,6-dihydro-2H-pyrane represented by the formula (IV) described above 4.74 g (44.6 mmol) of benzaldehyde, 1.53 g (22.3 mmol) of isoprene and 10 ml of dried toluene were fed into a 100 ml four neck flask equipped with a condenser, a thermometer and a stirrer. Then, 0.32 g (2.23 mmol) of $BF_3 \cdot O(C_2H_5)_2$ was added, and stirring was continued at room temperatures. After further stirring the mixture for 8 hours, it was cooled down and then poured into ice and water. The organic layer was separated, and the aqueous layer was washed with hexane. The collected organic layer was washed with an aqueous solution of sodium hydrogen carbonate and then with a saturated saline solution. The solvents were distilled off, and the residue was distilled under reduced pressure, whereby 1.99 g (yield: 51%) of the desired dihydropyrane compound was obtained.

Comparative Example 3
Preparation of 6-phenyl-4-methyl-5,6-dihydro-2H-pyrane represented by the formula (IV) described above 5.3 g (40 mmol) of aluminum chloride and 40 ml of n-hexane were fed into a 200 ml four neck flask equipped with a condenser, a thermometer and a stirrer. This mixture was cooled down to about −5° C., and then 3.56 g (40 mmol) of 2-nitropropane was added at this temperature in 10 minutes. Then, a mixture of 10.6 g (100 mmol) of benzaldehyde, 14.9 g (220 mmol) of isoprene and 30 ml of n-hexane was added dropwise in 30 minutes while stirring thoroughly at −5° C. After further stirring the mixture for 10 minutes at −5° C. and then poured into ice and water. The layers were separated, and the aqueous layer was washed with hexane. The collected organic layer was washed with an aqueous solution of sodium hydrogen carbonate and then with a saturated saline solution. The solvent was distilled off, and the residue was distilled under reduced pressure, whereby 9.38 g (yield: 54%) of desired dihydropyrane was obtained.

We claim:

1. A process for preparing a dihydropyrane compound (III) having the formula (III):

in which $R^1$ represents a hydrogen atom, an alkyl group or alkenyl group having 1 to 12 carbon atoms, a cycloalkyl group which may be substituted with alkyl group, having 3 to 12 total carbon atoms or an aryl group which may be substituted with alkyl group or alkoxy group, having 6 to 12 total carbon atoms; $R^2$ and $R^3$ may be same or different and each represents a hydrogen atom or an alkyl group or alkenyl group having 1 to 6 carbon atoms, which comprises the step of reacting an aldehyde compound (I) having the formula (I):

$$R^1\text{—CHO} \qquad (1)$$

in which $R^1$ is defined as above, with a diene compound (II) having the formula (II):

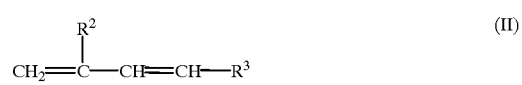

in which $R^2$ and $R^3$ are defined as above, in the presence of a Lewis acid and at least one co-catalyst selected from the group consisting of a base and a combination of a base and a compound (VIII) having a weaker coordination power to the Lewis acid than the aldehyde compound (I) and having an activity to dissolve the Lewis acid, coordinated by the compound (VIII), in a solvent.

2. The process as claimed in claim 1, in which the co-catalyst is a base.

3. The process as claimed in claim 1, in which the co-catalyst is a compound (VIII) selected from the group consisting of an aromatic or aliphatic ester compound, a chloro-acetic ester compound, an ether compound, a ketone compound and a carbonate compound.

4. The process as claimed in claim 1, in which the co-catalyst is a combination of a base with a compound (VIII).

5. The process as claimed in claim 1, in which the Lewis acid is selected from the group consisting of aluminum chloride, tin tetrachloride, iron trichloride, titanium trichloride, titanium tetrachloride and boron trifluoride.

6. The process as claimed in claim 2, in which the base is used in an amount of 0.01 to 1 mole per 1 mole of the Lewis acid.

7. The process as claimed in claim 1, in which the compound (VIII) is used in an amount of 0.1 to 10 moles per 1 mole of the Lewis acid.

8. The process as claimed in claim 4, in which the base is used in an amount of 0.01 to 1 mole per 1 mole of the Lewis acid and the compound (VIII) is used in an amount of 0.1 to 10 moles per 1 mole of the Lewis acid.

9. The process as claimed in claim 1, in which the co-catalyst is a combination of a base with a nitro compound as the compound (VIII).

10. The process as claimed in claim 1, in which the Lewis acid is boron trifluoride and the co-catalyst is an amine compound as the base.

11. The process as claimed in claim 1, in which the Lewis acid is aluminum chloride and the co-catalyst is methyl benzoate as the compound (VIII).

12. A process for preparing a dihydropyrane compound (III) having the formula

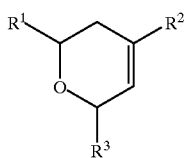

(III)

in which $R^1$ represents an alkyl group or alkenyl group having 1 to 12 carbon atoms, a cycloalkyl group which may be substituted with alkyl group, having 3 to 12 total carbon atoms or an aryl group which may be substituted with alkyl group or alkoxy group, having 6 to 12 total carbon atoms; $R^2$ and $R^3$ may be same or different and each represents a hydrogen atom or an alkyl group or alkenyl group having 1 to 6 carbon atoms, which comprises the step of reacting an aldehyde compound (I) having the formula (I):

  (1)

in which $R^1$ is defined as above, with a diene compound (II) having the formula (II):

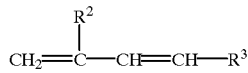  (II)

in which $R^2$ and $R^3$ are defined as above, in the presence of a Lewis acid and at least one co-catalyst, wherein the at least one co-catalyst is a compound (VIII) having a weaker coordination power to the Lewis acid than the aldehyde compound (I) and having an activity to dissolve the Lewis acid, coordinated by the compound (VIII), in a solvent, provided that the compound (VIII) is not a nitro compound.

13. The process as claimed in claim 12, in which the compound (VIII) is a member selected from the group consisting of an aromatic or aliphatic ester compound, a chloroacetic ester compound, an ether compound, a ketone compound and a carbonate compound.

14. The process as claimed in claim 12, in which the Lewis acid is selected from the group consisting of aluminum chloride, tin tetrachloride, iron trichloride, titanium trichloride, titanium tetrachloride and boron trifluoride.

15. The process as claimed in claim 12, in which the compound (VIII) is used in an amount of 0.1 to 10 moles per 1 mole of the Lewis acid.

16. The process as claimed in claim 12, in which the Lewis acid is aluminum chloride and the co-catalyst is methyl benzoate as the compound (VIII).

* * * * *